(12) United States Patent
Gruhlke

(10) Patent No.: US 6,956,221 B2
(45) Date of Patent: Oct. 18, 2005

(54) TUNABLE CROSS-COUPLING EVANESCENT MODE OPTICAL DEVICES AND METHODS OF MAKING THE SAME

(75) Inventor: Russell W. Gruhlke, Fort Collins, CO (US)

(73) Assignee: Agilent Technologies, Inc., Palo Alto, CA (US)

( * ) Notice: Subject to any disclaimer, the term of this patent is extended or adjusted under 35 U.S.C. 154(b) by 355 days.

(21) Appl. No.: 10/356,908

(22) Filed: Feb. 3, 2003

(65) Prior Publication Data

US 2004/0149928 A1     Aug. 5, 2004

(51) Int. Cl.[7] .............................................. G01N 21/64
(52) U.S. Cl. ................................ 250/458.1; 250/459.1
(58) Field of Search ........................... 250/458.1, 459.1

(56) References Cited

U.S. PATENT DOCUMENTS

| | | | |
|---|---|---|---|
| 4,882,288 A | | 11/1989 | North et al. |
| 4,971,426 A | * | 11/1990 | Schildkraut et al. ........ 359/247 |
| 5,006,716 A | | 4/1991 | Hall |
| 5,449,918 A | | 9/1995 | Krull et al. |
| 5,841,143 A | * | 11/1998 | Tuma et al. ............. 250/458.1 |
| 5,986,808 A | | 11/1999 | Wang |
| 6,504,651 B1 | * | 1/2003 | Takatori ..................... 359/640 |
| 6,738,194 B1 | * | 5/2004 | Ramirez et al. ........... 359/585 |
| 2002/0135293 A1 | * | 9/2002 | Aruga ....................... 313/493 |
| 2003/0164947 A1 | * | 9/2003 | Vaupel ....................... 356/445 |

OTHER PUBLICATIONS

Gruhlke et al., Surface Plasmon Cross Coupling in Molecular Fluorescence Near a Corrugated Thin Metal Film, Jun. 30, 1986, Physical Review Letters, col. 56, No. 23, pp. 2838-2841.*

* cited by examiner

*Primary Examiner*—David Porta
*Assistant Examiner*—Christine Sung

(57) ABSTRACT

Tunable cross-coupling evanescent mode optical devices and methods of making the same are described. In one aspect, a tunable optical device includes a first layer, a second layer, a metal layer disposed between the first and second layers, and an electrode. The first layer is supportable of electromagnetic field modes over a range of wavelengths that includes a target wavelength range. The second layer is disposed between the metal layer and the electrode and has an index of refraction that is adjustable over a range of values. The metal layer is disposed between the first and second layers and has at least one corrugated metal film region with a corrugation periodicity enabling cross-coupling of evanescent modes of equal wavelength within the target wavelength range and localized on opposite sides of the metal layer with different respective wavenumbers. The cross-coupling evanescent modes have a cross-coupling wavelength determined at least in part by the corrugation periodicity and the index of refraction of the first and second layers and is substantially unaffected by the electrode.

20 Claims, 2 Drawing Sheets

TUNABLE CROSS-COUPLING EVANESCENT MODE OPTICAL DEVICES AND METHODS OF MAKING THE SAME

BACKGROUND

Surface plasmon resonance occurs when radiant energy is "coupled" (or transferred) to electrons in a metal. The wavelength of light at which coupling occurs depends on the characteristics of the metal that is illuminated and the optical properties of the surrounding environment. When there is a match or resonance between the energy and wavenumber of the light photons and the electrons at the metal surface, a transfer of energy occurs. The coupling of light into a metal surface produces a plasmon (i.e., a group of excited electrons which behave like a single electrical entity). The plasmon, in turn, generates an electro-magnetic field that typically extends on the order of about 100 nanometers (nm) above and below the metal surface and oscillates with optical frequencies.

U.S. Pat. No. 5,841,143 has proposed a waveguide integrated fluorescence sensor that includes a corrugated dielectric-metal-dielectric thin film stack that is fabricated on a p-n junction. Fluorescent light of a single wavelength is selectively transmitted through the corrugated thin film stack and converted into an electronic signal by the p-n junction. Wavelength filtering is enabled by evanescent mode (or evanescent wave) cross-coupling across the metal film. Such cross-coupling includes cross-coupling between surface plasmons across the metal film and cross-coupling between surface plasmons and waveguide modes across the metal film.

SUMMARY

The invention features tunable cross-coupling evanescent mode optical devices and methods of making the same. The invention enables the wavelength of light transmitted through a corrugated metal layer to be readily changed based on selective adjustment of the index of refraction of a variable index layer in the vicinity of the corrugated metal layer.

In one aspect of the invention, a tunable optical device includes a first layer, a second layer, a metal layer disposed between the first and second layers, and an electrode. The first layer is supportable of electromagnetic field modes over a range of wavelengths that includes a target wavelength range. The second layer is disposed between the metal layer and the electrode and has an index of refraction that is adjustable over a range of values. The metal layer is disposed between the first and second layers and has at least one corrugated metal film region with a corrugation periodicity enabling cross-coupling of evanescent modes of equal wavelength within the target wavelength range and localized on opposite sides of the metal layer with different respective wavenumbers. The cross-coupling evanescent modes have a cross-coupling wavelength determined at least in part by the corrugation periodicity and the index of refraction of the first and second layers and is substantially unaffected by the electrode.

In another aspect, the invention features a method of making the above-described tunable optical device.

Other features and advantages of the invention will become apparent from the following description, including the drawings and the claims.

DETAILED DESCRIPTION

In the following description, like reference numbers are used to identify like elements. Furthermore, the drawings are intended to illustrate major features of exemplary embodiments in a diagrammatic manner. The drawings are not intended to depict every feature of actual embodiments nor relative dimensions of the depicted elements, and are not drawn to scale.

Figure 1:
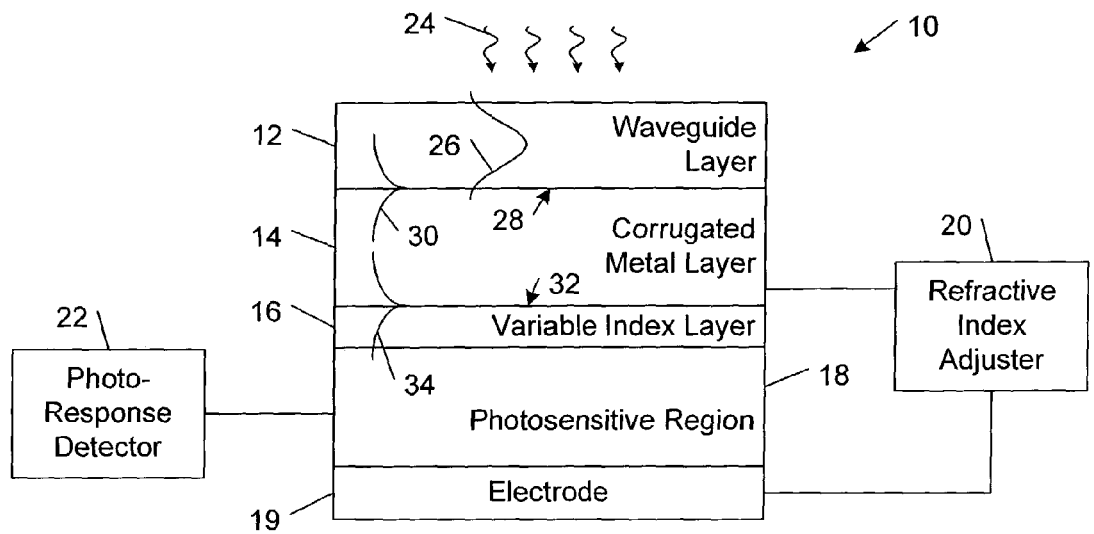
FIG. 1 is a block diagram of a tunable optical device that has a photosensitive region and an overlying thin film stack that includes a corrugated metal layer disposed between a waveguide layer and a layer with an adjustable index of refraction.

Referring to FIG. 1, in some embodiments, a tunable optical device 10 includes a waveguide layer 12, a corrugated metal layer 14, a layer 16 with an adjustable index of refraction, an optional photosensitive region 18, and an electrode 19. In some embodiments, tunable optical device 10 is formed by known thin film fabrication techniques.

Waveguide layer 12 is able to support electromagnetic field modes over a range of wavelengths that includes a target wavelength range. Waveguide layer 12 may be formed of any dielectric material, including silicon dioxide, silicon nitride, and lithium fluoride. In some embodiments, waveguide layer 12 has a thickness of about 200–500 nm.

Corrugated metal layer 14 is a continuous thin film layer that has a thickness between about 20 nm and 100 nm. Corrugated metal layer 14 may be formed of any thin metal film, including thin films of silver and gold. The corrugation periodicity (i.e., the spatial distance between adjacent corrugation peaks or adjacent corrugation valleys) of metal layer 14 is selected to enable cross-coupling of evanescent modes (or evanescent waves) of equal wavelength within the target wavelength range and localized on opposite sides of the metal layer 14 with different respective wavenumbers. As used herein, the term evanescent mode cross-coupling refers to cross-coupling between surface plasmons and cross-coupling between surface plasmons and waveguide modes. In one implementation, metal layer 14 has corrugations that are characterized by a peak-to-valley depth of about 50 nm and a corrugation periodicity of about 1.1 micrometer ($\mu$m). In this implementation, the cross-coupling wavelength range extends from about 850 nm to about 400 nm when the waveguide layer 12 has a refractive index of about 1.5 and the refractive index of a liquid crystal layer 16 is varied from about 1.5 to about 1.7. The cross-coupling wavelength range in this implementation may be extended by increasing the grating periodicity. In some embodiments, metal layer 14 is localized in separate discrete regions of tunable optical device 10. In some embodiments, tunable optical device 10 includes multiple separate metal film regions each of which is characterized by a different respective corrugation periodicity.

In some implementations, the corrugations of metal layer 16 are characterized by a sinusoidal surface relief. In these implementations, the corrugation may be achieved by patterning one of the underlying layers (e.g., variable index layer 16 or photo-sensitive region 18). For example, a photoresist layer may be spun on a planar surface of variable index layer 16 or photosensitive region 18. The photoresist is exposed to two interfering laser beams of the same wavelength. This causes a sinusoidal variation in the photoresist exposure. Upon development, the photoresist layer will have a sinusoidal surface relief with dimensions and periodicity corresponding to the desired corrugation peak-to-valley depth and the desired corrugation periodicity. The surface relief pattern may be transmitted into the variable index layer 16 or the photosensitive region 18 by etching (e.g., ion beam milling or dry chemical etching). If the sinusoidal surface relief is etched into the photosensitive region 18, the variable index layer 16 is formed on the etched photosensitive region 18 and the metal layer is formed on the variable index layer 16. The variable index layer 16 is sufficiently thin that the sinusoidal spatial variations are transferred from photosensitive region 18 to the overlying metal layer 14. If the sinusoidal surface relief is etched into the variable index layer 16, a metal film is simply formed on the variable index layer 16 to form the corrugated metal layer 14. Waveguide layer 12 is formed over the corrugated metal layer 14.

Variable index layer 16 may be formed of any dielectric or electro-optic material that has an index of refraction that may be varied controllably over a range of refraction index values that includes refraction index values that are different from the refraction index of waveguide layer 12. In some implementations, variable index layer 16 is formed of an electro-optic material. Exemplary electro-optic materials that may be used to form variable index layer 16 include: lithium niobate; lithium tantalite; potassium dihydrogen phosphate; potassium dideuterium phosphate; aluminum dihydrogen phosphate; aluminum dideuterium phosphate; barium sodium niobate; and liquid crystal. In these implementations, a refraction index adjuster 20 (e.g., a voltage source) is operable to apply a voltage between corrugated metal layer 14 and electrode 19. The applied voltage is sufficient to create across variable index layer 16 an electric field of sufficient strength to controllably adjust the refractive index of variable index layer 16. In some implementations, variable index layer 16 has a thickness between about 50 nm and 100 nm.

The optional photosensitive region 18 may be formed of any material that responds to electromagnetic fields within the target wavelength range with a detectable photo-response. In some implementations, photosensitive region 18 includes a conventional semiconductor p-n (or n-p) junction. In these implementations, a photo-response detector 22 (e.g., an electronic circuit) is operable to measure electrical responses of photo-sensitive region 18 to evanescent mode fields that are transmitted across corrugated metal layer 14 (e.g., measure an electrical current generated in the photosensitive region 18 or measure a change in voltage or resistance across the photosensitive region 18).

Electrode 19 may be formed of any electrically conducting material (e.g., a metal or indium-tin-oxide). Electrode 19 is configured so that it does not affect evanescent mode cross-coupling across metal layer 14. For example, in the illustrated embodiment, photosensitive region 18 prevents electrode 19 from influencing evanescent mode cross-coupling across metal layer 14. In some embodiments, electrode 19 is disposed between variable index layer 16 and photosensitive region 18. In these embodiments, electrode 19 is formed of a material (e.g., indium-tin-oxide for visible and ultraviolet wavelengths) that is substantially transparent to light within the target wavelength range.

In operation, incident radiation 24 couples into waveguide layer 12 by exciting surface plasmon modes supported at the metal/waveguide layer interface 28 or by exciting waveguide modes in the waveguide layer 12. Both surface plasmons and waveguide modes are evanescent modes whose electromagnetic fields 30 decay rapidly with increasing distance away from the metal layer/waveguide layer interface 32 and the center of the waveguide layer 26, respectively. Evanescent modes can also be supported at the variable index layer/metal layer interface 32 (surface plasmons) and in the variable index layer 16 (waveguide modes). If the media on opposite sides of the metal film have different values of refractive index, evanescent modes with the same wavelength and different wavenumbers, $k_z$, are supported on opposite sides of the corrugated metal layer. The presence of the corrugation allows wavenumber matching and, as a result, evanescent modes on one side of the corrugated metal layer can cross couple with evanescent modes with equal wavelength on the opposite side of the corrugated metal layer. In particular, surface plasmons with the same wavelength on opposite sides of the corrugated metal layer can cross couple. Also, surface plasmons and TM waveguide modes of equal wavelength and localized to opposite sides of the corrugated metal layer can cross couple. TE waveguide modes have an orthogonal polarization with respect to surface plasmons and, therefore, cannot interact with surface plasmons. As a consequence of the corrugation-induced cross coupling, radiative energy at the desired wavelength is transmitted across the otherwise opaque corrugated metal layer. The corrugation periodicity of the corrugated metal layer 14 and the indices of refraction of layers 12, 16 determine the wavelength at which the surface plasmons cross-couple across corrugated metal layer 14.

Figure 2:
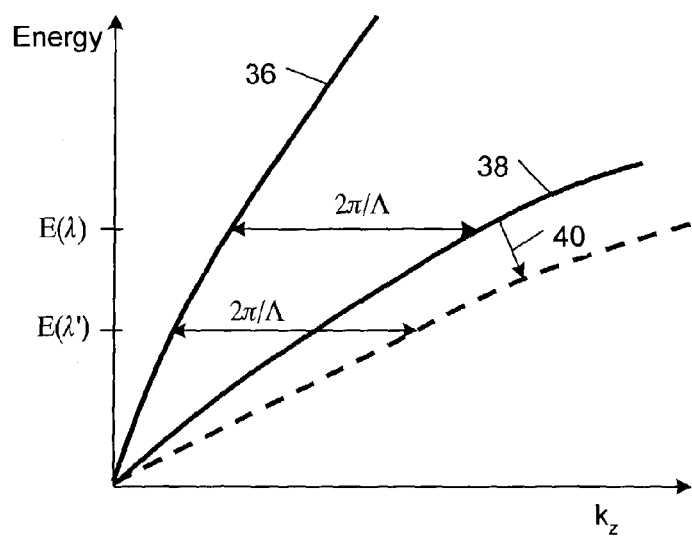
FIG. 2 is an exemplary graph of surface plasmon energy plotted as a function of wavenumber for the two metal interfaces of the tunable optical device of FIG. 1.

Referring to FIG. 2, in one illustrative example, at the wavelength λ, two surface plasmon states at opposite sides of the corrugated metal layer 14 couple when the wavenumbers ($k_z$) of the surface plasmon states that are parallel to the metal interfaces are matched via the corrugated metal layer 14. In particular, the presence of the corrugation contributes a wavenumber contribution, $\Delta k_z$, which is equal to $+/-2\pi n/\Lambda$, where $\Lambda$ is the corrugation periodicity and n is an integer having a value of 1 or more. Since the surface plasmon dispersion curves 36, 38 for surfaces 28, 32 of metal layer 14 are diverging, there is one and only one wavelength, λ, where wavenumber matching is accomplished. In the illustrated embodiment, if an electric field is applied across the variable index layer 16, the refractive index of this layer changes. For the purpose of this discussion, without loss of generality, it is assumed that the refractive index increases; although in some implementations, the refraction index of layer 16 may decrease in response to an applied electric field. As the refraction index increases, the surface plasmon dispersion curve 38 "rotates" (as shown by arrow 40) towards larger $k_z$ values. The cross-coupling wavelength is shifted to a longer wavelength λ' (i.e., lower energy; as shown) because the corrugation period has not changed. Thus, the radiation wavelength that is allowed to pass through the metal film and, hence, be detected varies as a function of the voltage applied across the variable index layer.

As explained in detail below, in some embodiments, the tunable optical device 10 may be implemented as an optical sensor that may be tuned to detect desired wavelengths of light by adjusting the voltage applied between the corrugated metal layer 14 and electrode 19. In other embodiments, the optional photosensitive region 18 may be omitted and the resulting tunable optical device may be used as a tunable optical wavelength filter.

Figure 3:
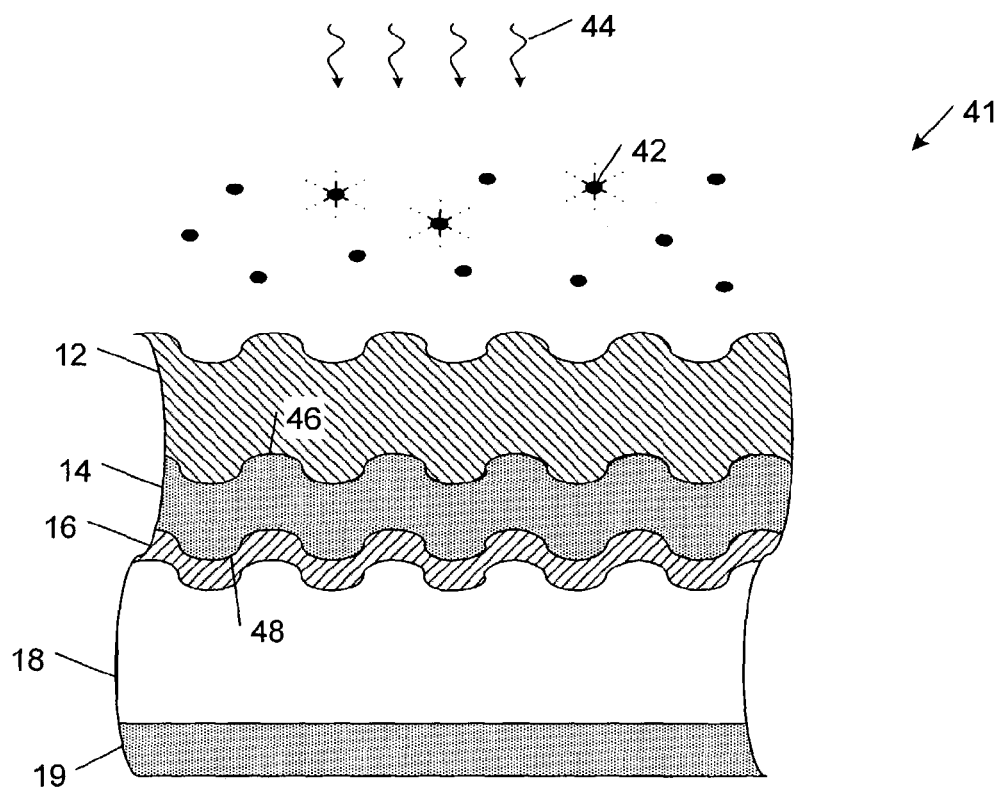
FIG. 3 is a diagrammatic view of an implementation of the tunable optical device of FIG. 1 that is operable to detect fluorescence that is emitted from fluorescent material disposed near the waveguide layer.

As shown in FIG. 3, in some embodiments, the tunable optical device of FIG. 1 may be implemented as a fluorescence sensor 41. In these embodiments, a fluorescent material 42 is placed adjacent to the waveguide layer 12 of the fluorescence sensor 41. The fluorescent material 42 may be in a gaseous, liquid, or solid state. Alternatively, a film of fluorescent material 42 may be deposited on a surface of waveguide layer 12. In operation, excitation radiation 44 is applied to the fluorescent material 42. The excitation radiation 44 may be delivered from either an external source or from light confined to the waveguide layer 12 via a waveguide mode. The excitation radiation 44 includes wavelengths that excite atoms or molecules of interest in the fluorescent material 12. The waveguide layer 12 supports the propagation of waveguide modes that generate a strong electromagnetic field in the vicinity of the fluorescent material 42, enhancing the intensity of fluorescent light that is generated by the fluorescent material 42.

Fluorescent light flows away from the fluorescent material 42 and into waveguide layer 12. The wavelength content of the resulting evanescent modes is the same as that of the fluorescent emission spectra of the fluorescing atoms or molecules in the fluorescent material 12. Surface plasmons at interface 46 between the waveguide layer 12 and corrugated metal layer 14 are excited at all fluorescent emission wavelengths. TM waveguide modes in the waveguide layer 12 also are excited at all fluorescent wavelengths. Based on the refractive index to which variable index layer 16 is adjusted, surface plasmons or TM waveguide modes (or both) of a desired cross-coupling wavelength are supported at both metal interfaces 46, 48 and layers 12, 16 respectively. Thus, only fluorescent light at the desired wavelength is transmitted through the corrugated metal layer 14 to the photosensitive region 18.

Figure 4:
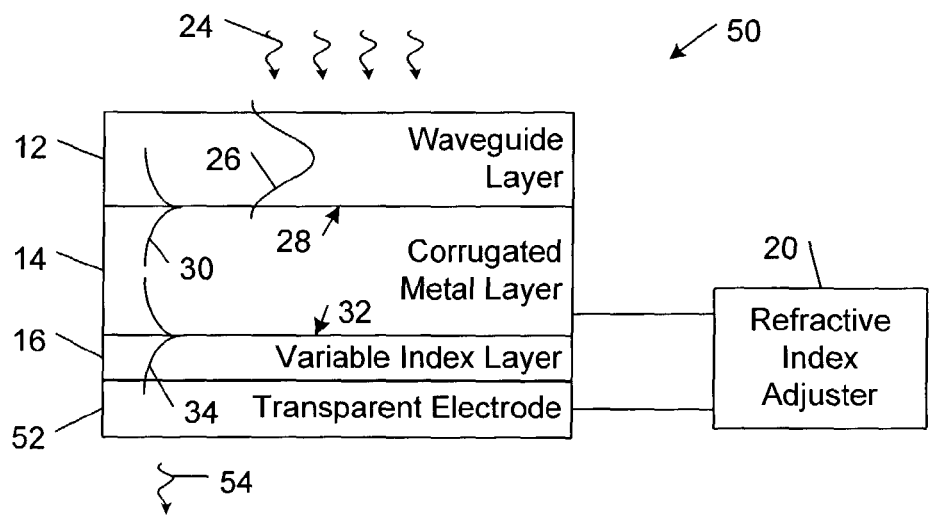
FIG. 4 is a block diagram of a tunable optical device that has a thin film stack that includes a corrugated metal layer disposed between a waveguide layer and a layer with an adjustable index of refraction.

Referring to FIG. 4, in some embodiments, a tunable optical wavelength filter 50 may be implemented by forming the multi-layer stack 12–16 on an electrode 52 that is substantially transparent to radiation within the target wavelength range. In operation, only radiation 54 that has a wavelength corresponding to the tuned evanescent mode cross-coupling wavelength is able to pass though tunable optical wavelength filter 50.

Other embodiments are within the scope of the claims.

What is claimed is:

1. A tunable optical device, comprising:
   a first layer supportable of electromagnetic field modes over a range of wavelengths that includes a target wavelength range;
   a second layer having an index of refraction adjustable over a range of values;
   a metal layer disposed between the first and second layers and including at least one corrugated metal film region with a corrugation periodicity enabling cross-coupling of evanescent modes of equal wavelength within the target wavelength range and localized on opposite sides of the metal layer with different respective wavenumbers, the cross-coupling evanescent modes having a cross-coupling wavelength determined at least in part by the corrugation periodicity and the index of refraction of the first and second layers; and
   an electrode, wherein the second layer is disposed between the metal layer and the electrode and the cross-coupling wavelength is substantially unaffected by the electrode.

2. The tunable optical device of claim 1, wherein the second layer comprises an electro-optic material.

3. The tunable optical device of claim 2, wherein the electro-optic material includes one or more of the following materials: lithium niobate; lithium tantalite; potassium dihydrogen phosphate; potassium dideuterium phosphate; aluminum dihydrogen phosphate; aluminum dideuterium phosphate; barium sodium niobate; and liquid crystal.

4. The tunable optical device of claim 2, further comprising a refractive index adjuster electrically connected to the metal layer and the electrode and operable to apply different electric fields across the second layer.

5. The tunable optical device of claim 1, wherein the corrugated metal film region has a thickness between about 20 nm and about 100 nm.

6. The tunable optical device of claim 5, wherein the first layer has a dielectric constant of about 1.5, the second layer is formed of liquid crystal, and the corrugated metal film region has corrugations characterized by a peak-to-valley depth of about 50 nm and a corrugation periodicity of about 1.1 $\mu$m, the cross-coupling wavelength being variable from about 850 nm to about 400 nm when the refractive index of the second layer is varied from about 1.5 to about 1.7.

7. The tunable optical device of claim 1, wherein the metal layer includes multiple metal film regions each characterized by a different respective corrugation periodicity.

8. The tunable optical device of claim 1, wherein the metal layer is substantially opaque to light outside the target wavelength range.

9. The tunable optical device of claim 1, further comprising a photosensitive region disposed adjacent to the electrode.

10. The tunable optical device of claim 9, further comprising a photo-response detector electrically connected to the photosensitive region.

11. The tunable optical device of claim 1, further comprising a fluorescent material, wherein the first layer is supportable of electromagnetic field modes at wavelengths corresponding to fluorescence and absorption wavelengths of the fluorescent material, wherein the supported electromagnetic field modes penetrate into the fluorescent material to enhance fluorescence of the fluorescent material.

12. The tunable optical device of claim 11, wherein the second layer comprises an electro-optic material.

13. The tunable optical device of claim 11, wherein the fluorescent material is disposed over a surface of the first layer.

14. The tunable optical device of claim 11, further comprising a photosensitive region responsive to fields produced by evanescent modes excited at the second surface of the metal layer.

15. The tunable optical device of claim 14, wherein the electrode is formed of indium-tin-oxide.

16. The tunable optical device of claim 1, wherein the electrode is substantially transparent to radiation within the target wavelength range.

17. A method of making a tunable optical device, comprising:

forming a first layer supportable of electromagnetic field modes over a range of wavelengths that includes a target wavelength range;

forming a second layer having an index of refraction adjustable over a range of values;

forming a metal layer between the first and second layers and including at least one corrugated metal film region with a corrugation periodicity enabling cross-coupling of evanescent modes of equal wavelength within the target wavelength range and localized on opposite sides of the metal layer with different respective wavenumbers, the cross-coupling evanescent modes having a cross-coupling wavelength determined at least in part by the corrugation periodicity and the index of refraction of the first and second layers; and forming an electrode, wherein the second layer is disposed between the metal layer and the electrode and the cross-coupling wavelength is substantially unaffected by the electrode.

18. The method of claim 17, wherein the second layer comprises an electro-optic material.

19. The method of claim 17, further comprising forming a photosensitive region disposed between the electrode and the second layer.

20. The method of claim 19, further comprising forming a fluorescent material layer over the first layer.

* * * * *